United States Patent [19]

Takahashi

[11] Patent Number: 4,492,475

[45] Date of Patent: Jan. 8, 1985

[54] METHOD OF DETECTING FOREIGN MATTERS MIXED IN A LIQUID CONTAINED IN TRANSPARENT RECEPTACLES AND APPARATUS RELEVANT THERETO

[75] Inventor: Toshio Takahashi, Honjo, Japan

[73] Assignee: Eisai Co., Ltd., Tokyo, Japan

[21] Appl. No.: 353,794

[22] Filed: Mar. 2, 1982

[51] Int. Cl.³ .............................................. G01N 21/90
[52] U.S. Cl. .................................... 356/427; 356/240
[58] Field of Search ..................... 356/427, 428, 240; 250/227; 350/96.31

[56] References Cited

U.S. PATENT DOCUMENTS

| 3,029,349 | 4/1962 | Schell ................................. 356/427 |
| 3,737,236 | 6/1973 | Borrelli ....................... 350/96.31 X |
| 4,028,553 | 6/1977 | Farcinade ...................... 356/427 X |
| 4,058,737 | 11/1977 | Takahashi et al. ............. 356/427 X |
| 4,087,184 | 5/1978 | Knapp et al. ......................... 356/427 |

OTHER PUBLICATIONS

"Optical Characteristics Of A Light-Focusing Fiber Guide And Its Applications"; Uchida et al.; IEEE Jour. Of Quantum Electronics, vol. QE6, No. 10, Oct. 1970, pp. 606-612.

*Primary Examiner*—Vincent P. McGraw
*Attorney, Agent, or Firm*—Flynn, Thiel, Boutell & Tanis

[57] ABSTRACT

A method of detecting foreign matters mixed in a liquid filled in a transparent receptacle, which comprises bringing said receptacle to a sudden stop after rotating it at high speed, subjecting the receptacle to light by means of a projector disposed outside the receptacle to thereby expose foreign matters floating in the liquid contained in the receptacle to rays of light, making the ray-receiving surface of a ray receiver disposed on the opposite side of the projector relative to the receptacle receive the flux of light passing through the receptacle by way of light-focusing glass fibers provided for the ray receiver, and detecting foreign matters mixed in the liquid on the basis of the decrease or increase in the amount of rays received.

4 Claims, 5 Drawing Figures

METHOD OF DETECTING FOREIGN MATTERS MIXED IN A LIQUID CONTAINED IN TRANSPARENT RECEPTACLES AND APPARATUS RELEVANT THERETO

BACKGROUND OF THE INVENTION

The present invention relates to a method of detecting foreign matters mixed in a liquid contained in a transparent receptacle, coupled with an apparatus relevant thereto. To be more precise, it relates to a method of detecting undesirable, minute foreign matters that might be present within an air-tight transparent receptacle such as ampules filled with liquid medicine, as well as an apparatus relevant thereto.

Heretofore, as an art of this kind for the purpose of detecting foreign matters, there is known a method employing an apparatus which is devised as follows: transparent receptacles filled with a liquid are placed at regular intervals on the periphery of a turntable which rotates continuously as elucidated later on, and these receptacles are brought to a sudden stop after turning at high speed on the turntable during its rotation, whereby foreign matters mixed in the liquid are made to float; rays of light are applied to each of the thus stopped receptacles at almost a right angle by means of a projector which is installed outside the receptacle and repeats reciprocating motion of rapidly returning after moving by a fixed distance synchronously with the receptacle, and the flux of light transmitted to the outside of the receptacle is received by the ray-receiving surface of a ray receiver which is installed on the opposite side of the projector relative to the receptacle and moves synchronously with the projector; thus, when there occurs any decrease in the amount of light in respect of the image formed on the ray-receiving surface due to interruption of the light by foreign matters in the course of its transmission through the liquid, it is to be detected and the presence of foreign matters is thereby detected.

In an apparatus of this type, the projector is provided with a condenser lens for projecting parallel rays to the receptacle, while the ray receiver is provided with a focusing lens for focusing that parallel rays transmitted through the receptacle. As a focusing lens for this purpose, a lens set for use in ordinary cameras as lens system that displays a sufficient resolution even on minute foreign matters having a particle size of 50μ or thereabouts has been used. In this context, said focusing lens is required to be capable of not only forming a distinct image of minute foreign matters on the ray-receiving area but catching the whole flux of light given out from a light source and transmitted through the receptacle to make the brightness of the background as high and uniform as possible in order to improve the inspecting sensitivity, and therefore it has hitherto been unavoidable to employ a focusing lens having an aperture larger than the depth of the liquid within the receptacle.

As a consequence, the prior art is defective in that, though it is possible to perform the inspection by the use of an ordinary lens set of about 40 mm in aperture having a focal distance of, for instance, f55/F1.4 in the case of ampules of 2 ml or 5 ml, it is extremely difficult to materialize a focusing lens having a sufficient resolution on minute foreign matters and an adequate aperture for use in inspecting a receptacle wherein the depth of the liquid is 100 mm or more, such as 500 ml liquid supply bottle.

Besides, the prior art is defective in that, employment of a focusing lens having a large aperture necessitates provision of a considerably wide space between the focusing lens and the ray-receiving surface, entailing requirement for enlargement of the ray receiver as a whole that is not only difficult to design but apt to cause oscillation of the apparatus at the time of reciprocating motion during the inspection and bring about blurring of the resulting image. To be more precise, in the case where a lens having a focal distance of 135 mm, for instance, is employed, in order to obtain an equimultiplied image, it is necessary to make the distance between the receptacle and the lens and that between the lens and the ray-receiving surface twice longer than the foregoing focal distance, or 270 mm. Accordingly, the distance between the receptacle and the ray-receiving surface is required to be 540 mm and the size of the resulting ray receiver becomes large, entailing the foregoing defects.

Moreover, in the case of a transparent receptacle whose bottom makes a right angle with the side wall thereof (for example through a curved corner portion as shown in FIG. 5 herein), when parallel rays are projected to the receptacle at almost a right angle as in the foregoing, the incident rays are refracted at a large angle by the bottom of receptacle to hamper the transmission of flux of light through the liquid within the bottom portion, entailing a defect that foreign matters which might be present in said portion can not be detected.

SUMMARY OF THE INVENTION

One object of the present invention is to provide a method of detecting foreign matters mixed in a liquid filled in transparent receptacles and an apparatus relevant thereto, which can eliminate the afore described defects of conventional detecting methods and apparatuses, make it possible to receive uniformly flux of light coming through any portion of the receptacle even when the size of receptacle is enlarged, never bring about difference of brightness of the resulting image according to the portions of receptacle, and contribute to making the apparatus compact.

According to the present invention, the foregoing object can be achieved by providing a method and a relevant apparatus which are so devised that the flux of light projected to a receptacle from a projecting means installed outside the receptacle and transmitted through the receptacle and a liquid contained therein in the same way as in the prior art can be transferred to a ray-receiving surface through a multiplicity of light-focusing glass fibers provided within a ray-receiving means unlike the prior art.

Another object of the present invention is to provide a method of detecting foreign matters mixed in a liquid filled in transparent receptacles and an apparatus relevant thereto, which are so devised that the flux of light can be transmitted through a liquid within a transparent receptacle even in the case where the bottom of said receptacle makes a right angle with the side wall thereof (for example through a curved bottom cover as in FIG. 5 herewith) and the thus transmitted flux of light can be received by the light-focusing glass fibers of a ray-receiving means and transferred to the ray-receiving surface.

According to the present invention, the foregoing object can be achieved by providing an apparatus which is devised such that rays of light are to be projected aslant from a projecting means toward the bottom portion of the receptacle and light-focusing glass fibers of a ray-receiving means are disposed on the opposite side of the thus slanted projecting means relative to the receptacle in such a manner as to make the optic axes of said rays of light agree with the optic axis of the transmitted flux of light outside the receptacle.

A further object of the present invention is to provide a method and an apparatus relevant thereto which are capable of exactly detecting the presence of foreign matters mixed in a liquid with almost the same clearness whether they be in the central portion or the peripheral portion of the receptacle even when the receptacle is considerably large-sized.

According to the present invention, the foregoing object can be achieved by providing an apparatus which is devised such that a couple of inspection sets, each set consisting of projecting means and ray-receiving means, are so arranged as to make fellow projecting means and fellow ray-receiving means of each set form a V-shape respectively, the optic axes of flux of light in the respective sets cross each other at the center of the receptacle, and the focal distances of the light-focusing glass fibers of the ray-receiving means in each set vary with the use for inspection of the central portion and the use for inspection of the peripheral portion of the receptacle.

The exact nature of the present invention, as well as other objects and advantages thereof, will be readily apparent from consideration of the following specification relating to the accompanying drawings, in which like reference characters designate the same or similar parts throughout the figures thereof.

DETAILED DESCRIPTION OF THE INVENTION

In the embodiment of the present invention illustrated in FIGS. 2 through 5, parts other than the projectors 17 and 17' and the ray receivers 18 and 18' in the first inspection means 9 and the second inspection means 11 belong to well-known arts. Therefore, some of them that are of no particular importance are herein omitted from illustration, and also as to other well-known parts than the above defined, explanation thereof will be simplified.

First, the well-known parts in the present embodiment will be explained.

Figure 2:
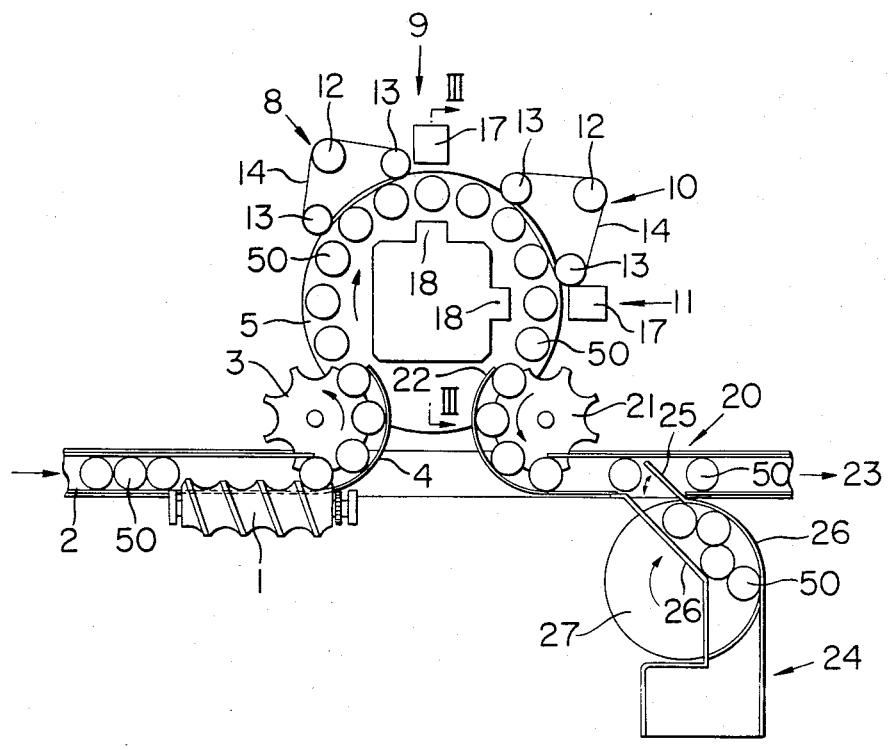
FIG. 2 is a plan of the whole of an embodiment of the foreign matter detecting apparatus according to the present invention.
Figure 3:
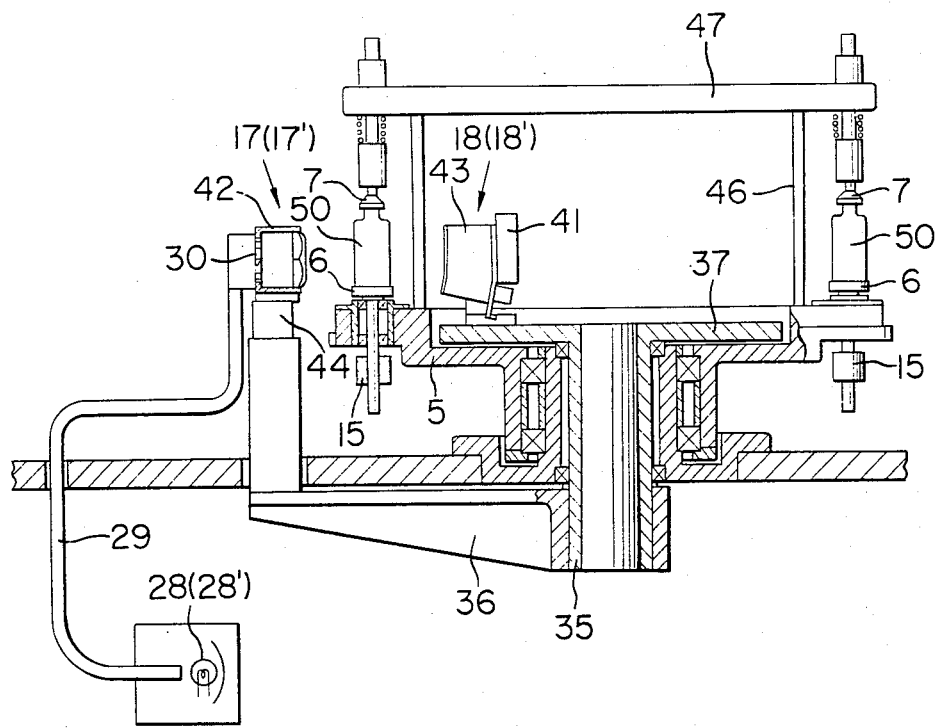
FIG. 3 is an enlarged cross-section of the apparatus shown in FIG. 2 as partially cut vertically along the line III—III thereof.

Referring to FIGS. 2 and 3, the reference numeral 1 denotes a screw feeder which supplies receptacles loaded on a belt conveyor 2 to a star wheel 3. The receptacles 50 supplied to the notches of the star wheel 3 are guided by a guide plate 4 with the rotation of the star wheel 3 to be supplied to seats 6 of a turntable 5.

The turntable 5 rotates continuously and synchronously with the star wheel 3, and the receptacles 50 supplied to the seats 6 of this turntable 5 are firmly held by caps 7 which hang in vertically movable fashion from a supporting plate 47 mounted on posts 46 erected on the turntable 5. On the periphery of the turntable 5 there are installed the first turning means for receptacle 8, the first inspection means 9, the second turning means for receptacle 10 and the second inspection means 11, and the first and second turning means for receptacle are respectively provided with a motor 12, a pulley 13 and a belt 14. This belt 14 comes in contact with a pulley 15 fixed on the supporting shaft of the seat 6 supported on the turntable 5 in rotatable fashion, and rotates the receptacle 50 at high speed.

Figure 5:
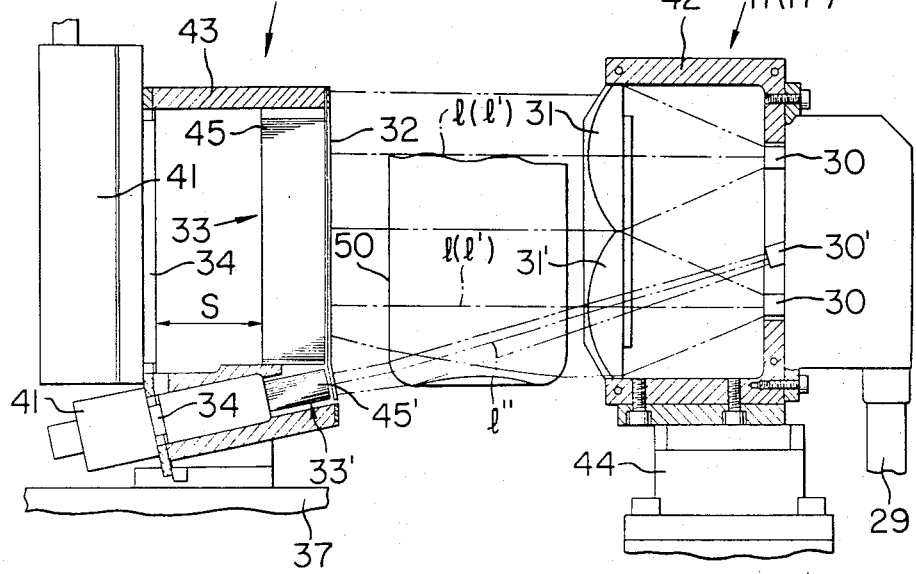
FIG. 5 is an enlarged cross-section of the figure shown in FIG. 4 as partially cut vertically along the line V—V thereof.

The first and second inspection means 9 and 11 are respectively equipped with a projector 17 and a ray receiver 18. This projector 17 is, as illustrated in FIGS. 3 and 5, provided with a lens case 42 which accommodates condenser lenses 31, 31' disposed in the front part thereof and projection heads 30 disposed in the rear part thereof to confront the respective lenses. This lens case 42 is disposed outside the turntable 5 and mounted on a case seat 44 fixed on the upper end of an L-shaped arm 36 which projects sideways from a shaft 35 installed in rotatable fashion relative to the turntable 5. Meanwhile, the projection head 30 is connected to a lamp 28 through a light transmit means 29. The thus devised projector 17 is disposed almost horizontally so as to be capable of projecting rays of light in almost normal direction toward the receptacle 50.

Figure 4:
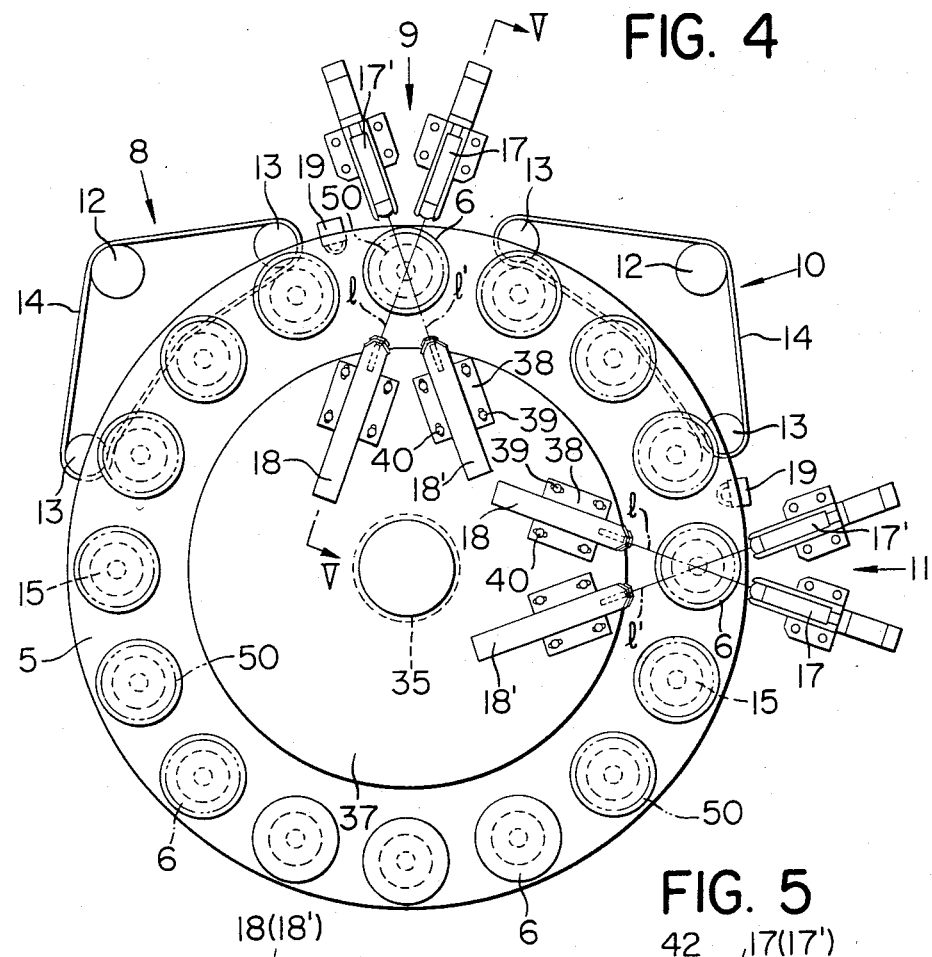
FIG. 4 is an enlarged detail plan of a part of the illustration in FIG. 2.

The ray receiver 18 is installed on a seat 38 mounted on a table 37 fixed to the upper end of a shaft 35 and is so devised that the position thereof can be freely adjusted both forward and backward by virtue of engagement of slits 39 and bolts 40 (cf. FIG. 4).

The above described projector and ray receiver are disposed to be opposite to each other with a receptacle 50 supported on the turntable 5 between them.

Further, between the first turning means for receptacle 8 and the first inspection means 9 there is provided a brake 19 for the purpose of bringing the receptacle 50 rotating as shown in FIG. 4 to a halt as it comes in contact with the pulley 15. Accordingly, when a receptacle held by a cap 7 disposed thereabove reaches the first turning means for receptacle 8 with the rotation of the turntable 5, the belt 14 and the pulley 15 come in contact with each other and rotate at high speed, whereby the receptacle 50 rotates together with the seat 6. When the receptacle passes through the first turning means for receptacle 8, the brake 19 comes in contact with the pulley 15 and brings the seat 6 to a halt. At this, the receptacle also comes to a halt, but minute foreign matters mixed in the liquid contained therein keep floating.

When the receptacle reaches the first inspection means 9, the table 37 moves synchronously with the turntable 5 by virtue of a reciprocating device not shown in the drawings and accordingly the projector 17 and the ray receiver 18 move together with the receptacle 50, whereby inspection of the content of receptacle is performed.

This inspection has been explained in detail in Japanese Laid-Open Patent Application No. 139597/1978 submitted previously by the applicant of the present invention. To give an epitome of the inspection hereunder, the flux of light transmitted through the receptacle 50 is focused by a focusing lens not shown herein and is formed into an image on a bundle of optical fibers that forms a ray-receiving surface disposed in the rear of said lens. The thus formed image is then transferred by way of said bundle of optical fibers to photoelectric elements disposed in the rear thereof, and by observing increase and decrease of the luminous intensity through the output from the photoelectric element the presence of foreign matters is to be detected. When the inspection is completed in this way, the first inspection means 9 returns rapidly to its former position and performs inspection of the suceeding receptacles.

The receptacle 50 subjected to the first inspection further moves with rotation of the turntable 5 and undergoes the second inspection by the second inspection means 11 in the same way as the first inspection by way of the second turning means 10.

Based on the results of the foregoing first and second inspections, the receptacles filled with a liquid 50 are classified into qualified goods and inferior goods by a succeeding selecting means 20 (cf. FIG. 2). Transfer of said receptacles 50 from the turntable 5 to this selecting means 20 is performed by a delivery star wheel 21, whose structure is the same as that of the aforesaid star wheel 3, together with the guide plate 22.

The selecting means 20 is equipped with a damper 25 for the purpose of sifting inferior goods to be sent to a delivery portion for inferior goods 23 from qualified goods to be sent to a delivery portion for qualified goods 24 with respect to the respectacles 50 transported by the conveyor 2, and this damper 25 works in accordance with instructions from the inspection means 9 and 11.

The delivery portion for qualified goods 24 comprises a guide plate 26 and a turntable 27.

The foregoing processes of the conventional method of detecting foreign matters are admittedly to be followed in the present invention in almost the same manner, but the point of difference between the method proposed in the present invention and the conventional method relates to the construction of the projector and ray receiver as well as the disposition thereof, so this characteristic of the present invention will be hereunder elucidated by reference to the embodiment illustrated in the accompanying drawings.

Referring to FIGS. 3 through 5, the first and second inspection means 9 and 11 are respectively provided with another projector 17' in addition to the afore described projector 17, said projector 17' being of the same construction, having optic axis "l'" which intersects the optic axis "l" of rays of light emitted from the projector 17 at the center of the receptacle 50 and being so disposed as to form a V-shape with the projector 17 relative to said center of receptacle. In concert with this provision of projector 17', another ray receiver 18' having the same construction as the ray receiver 18 for the purpose of receiving the flux of light emitted from the projector 17' is so disposed as to form a V-shape with the ray receiver 18 relative to the center of receptacle. The purpose in providing two sets of inspection means consisting of projector and ray receiver as set forth above is to facilitate the inspection of the central portion of the receptacle 50 by means of one set consisting of, for instance, the projector 17 and the ray receiver 18 and the inspection of the peripheral portion of the receptacle 50 by means of the other set consisting of the projector 17' and the ray receiver 18'. In this respect further elucidation will be made later on.

As regards the projectors 17 and 17', the construction of a portion thereof is different from that of the aforesaid conventional one. This point of difference lies in that, as seen from FIG. 5, one projection head 30 is disposed almost horizontally relative to the receptacle 50 like the conventional one, while the other projection head 30' is disposed aslant downward, preferably in such a manner as to make the optic axis "l'''" of rays of light pass through the lens 31' aslant downward at an angle of about 15° relative to a horizontal level, and thus, as seen in FIG. 5, the optic axis "l'''" is spaced above the curved bottom corner of the receptacle where it enters the near (right) sidewall of the receptacle but passes directly through the curved bottom corner of the receptacle at the bottom of the far (left) sidewall of the receptacle. By so disposing the optic axis "l", it becomes possible to inspect the bottom portion of the receptacle 50 in concert with the ray receivers 18 and 18' described below.

Further, in the ray receivers 18 and 18', in lieu of a single focusing lens employed for the conventional ray receiver, a multiplicity of light-focusing glass fibers 45 and 45' as disposed parallel to one another (cf. FIG. 5) are set within a frame 32 to thereby construct focusing lenses 33 and 33', and the lens 33 is disposed face to face with the projection head 30 while the lens 33' is disposed face to face with the projection head 30'. And, at a fixed distance S in the rear of these lenses 33 and 33' there is provided a ray-receiving surface 34 like in the prior art and further in the rear of this ray-receiving surface there are provided photoelectric elements (not shown in the drawing) as accommodated in a casing 41.

Figure 1:
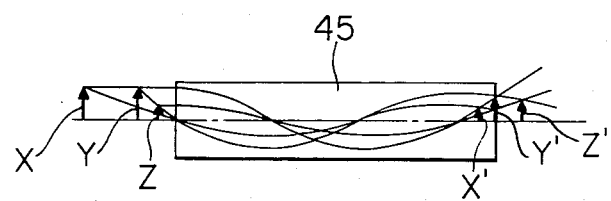
FIG. 1 is an illustration for explaining the optical properties of the light-focusing glass fibers.

The foregoing light-focusing glass fiber 45 is a kind of unistructural glass fiber popular under the trade name "Selfoc", and the radial refractive index of the rays of light transmitted lengthwise is to change continuously excepting that the rays of light incident upon the optic axis are to go straight on. Accordingly, as illustrated in FIG. 1, in the case of objects "X, Y, Z" located in different positions on the optic axis, rays of light projected from these objects mender along the optic axis to come to form an image respectively at different places along the lengthwise direction of the optic axis, such as denoted by "X', Y', Z'". Therefore, by the use of this glass fiber 45 cut into pieces of an appropriate length, there can be provided a lens having a focal distance corresponding to said length. Also, by virtue of arranging such pieces in proportion to the length of field of vision, there can be provided a lens having a wide field of vision or a lens having a short focal distance while being capable of functioning like conventional lenses of large aperture.

In the foregoing embodiment, by virtue of utilizing the optical characteristics of said optical fiber 45 such as described above, it also has become possible to perform inspection of the central portion and the peripheral portion of a receptacle separately as stated above.

For example, in the case of a receptacle 50 having a large diameter such as liquid supply bottles containing 200 ml, 500 ml and the like, detection of foreign matters floating in the peripheral portion of the receptacle can not be performed satisfactorily by merely focusing on one point of the central portion thereof. In view of this fact, two sets of projectors and ray receivers are installed as above, and at the time of inspecting the central portion by the ray receiver 18 and the peripheral portion by the ray receiver 18' with respect to a receptacle containing, for instance, 500 ml of liquid, as optical fiber 45 for the former receiver 18, fibers having a length corresponding to f50 mm are employed, while as optical fiber 45 for the latter receiver 18', fibers having a length corresponding of f50 mm are employed. The result of detection conducted by the use of the thus devised apparatus has proved very satisfactory.

Although a particular preferred embodiment of the invention has been disclosed in detail for illustrative purposes, it will be recognized that variations or modifications of the disclosed apparatus, including the arrangement of parts, lie within the scope of the present invention.

What is claimed is:

1. An apparatus for detecting foreign matters mixed in liquid in an upstanding transparent receptacle, including receptacles of the kind having a generally cylindrical sidewall and a bottom wall joined generally at right angles to said sidewall through a curved bottom corner portion, said apparatus comprising means for bringing a receptacle filled with liquid to a sudden stop after rotating at high speed, means disposed adjacent one side of the receptacle for projecting rays of light through the thus-stopped receptacle to expose foreign matters in floating state within the liquid contained in the receptacle to rays of light, ray receiving means disposed opposite to said projecting means relative to the receptacle for receiving rays of light transmitted through the receptacle, and means for detecting foreign matters mixed in the liquid by sensing the decrease in the amount of rays received by the ray receiving means, said projecting means comprising a first projecting head disposed in the upper part of said projecting means for projecting rays of light along a first optic axis through the upper portion of the receptacle at a first angle thereto which is almost a right angle and a second projecting head disposed in the lower part of said projecting means, said ray receiving means comprising first and second receivers each including a ray receiving surface and a corresponding ray focusing lens aligned therewith, each focusing lens being composed of a bundle of a multiplicity of light focusing glass fibers arranged in parallel with the optic axis of such lens, said second projecting head being aimed divergently from said first projecting head to project rays of light aslant downward through the lower portion of the receptacle along an optic axis at a second angle thereto and diverging from said first optic axis, said downward aslant optic axis of said second projecting head passing through the curved bottom corner portion of the receptacle at the circumferential segment thereof furthest from said second projecting head and closest to said second receiver for illuminating such curved bottom corner portion, said focusing lens and the ray receiving surface of said first and second receivers being aligned along different directions so as to respectively face generally horizontally toward the first projecting head and upward aslant toward the outside of said circumferential segment of said curved bottom portion of said receptacle.

2. A detecting apparatus according to claim 1 including two sets of projecting means and ray receiving means, fellow projecting means and ray receiving means of the two sets being oriented to form a pair of opposed V-shapes as seen from above, the optic axes of the two sets intersecting in the center of the receptacle, the focal distance of the light focusing glass fibers in one said set being arranged for inspection of the central portion of the receptacle and the focal distance of the light focusing glass fibers in the other set being arranged for inspection of the peripheral portion of the interior of the receptacle, such that the focal distances of the light focusing glass fibers of one set differ from that of the other set.

3. A detecting apparatus according to claim 1 in which the projecting means includes a third projecting head disposed beneath said first and second projecting heads, said third projecting head being oriented for projecting rays of light through the lower portion of the receptacle at almost a right angle thereto and substantially in parallelism with the first projecting head, said second projecting head being oriented convergently of said third projecting head to project rays of light downward through the lower portion of the receptacle convergently of rays from said third projecting head, said projecting means including lens means applying light rays from said first and third projecting heads substantially as vertically wide, vertically adjacent, parallel, and generally horizontal light beams impinging on the sidewall of the receptacle in an area extending upward from the bottom thereof, the light rays from said second projecting head forming a beam which is relatively narrow vertically and impinges on the near sidewall of the receptacle in spaced relation above the bottom thereof, said second angle being such as to allow passage of said beam from said second projecting head through said bottle to illuminate the remote circumferential part of the curved bottom corner portion of the receptacle, so as to illuminate the curved bottom corner portion of the receptacle despite any tendency of the light beam from the lower third projecting head to be bent upward by the near part of the curved bottom corner portion of the receptacle and away from the bottom of the receptacle.

4. A detecting apparatus according to claim 1 including a relatively large receptacle of about 500 ml size, in which the focusing lens of said first receiver is located close beside said receptacle and has its light-focusing optic fibers cut to a length corresponding to the focal length of said lens formed by said focusing optic fibers, which length is about 50 mm and thus small compared to the average of receptacle height and diameter, said lens being of large aperture and wide field of vision corresponding to the large size of the relatively large receptacle with such lens and the corresponding light receiving surface located relatively close to the receptacle as permitted by the shortness of lens focal length relative to lens aperture and field of vision and receptacle size.

* * * * *